(12) United States Patent
Huston et al.

(10) Patent No.: US 10,285,654 B2
(45) Date of Patent: May 14, 2019

(54) SYSTEM AND METHOD FOR DISPLAYING VARIABLE DURATION IMAGE SCANS

(71) Applicant: General Electric Company, Schenectady, NY (US)

(72) Inventors: Jeremy Huston, Brookfield, WI (US); David Littlejohn, Wales, WI (US); Scott Wollenweber, Waukesha, WI (US); Joseph Muth, Eagle, WI (US)

(73) Assignee: General Electric Company, Schenectady, NY (US)

( * ) Notice: Subject to any disclaimer, the term of this patent is extended or adjusted under 35 U.S.C. 154(b) by 1003 days.

(21) Appl. No.: 14/729,375

(22) Filed: Jun. 3, 2015

(65) Prior Publication Data

US 2016/0354047 A1 Dec. 8, 2016

(51) Int. Cl.
*A61B 5/05* (2006.01)
*A61B 6/04* (2006.01)
*A61B 6/00* (2006.01)
*A61B 6/03* (2006.01)
*A61B 90/00* (2016.01)

(52) U.S. Cl.
CPC .......... *A61B 6/0457* (2013.01); *A61B 6/0407* (2013.01); *A61B 6/465* (2013.01); *A61B 6/5205* (2013.01); *A61B 6/5264* (2013.01); *A61B 6/5288* (2013.01); *A61B 6/032* (2013.01); *A61B 6/037* (2013.01); *A61B 2090/374* (2016.02)

(58) Field of Classification Search
CPC ... A61B 6/0457; A61B 6/5288; A61B 6/5264; A61B 6/5205; A61B 6/0407; A61B 6/465; A61B 2090/374; A61B 6/037; A61B 6/032
See application file for complete search history.

(56) References Cited

U.S. PATENT DOCUMENTS

| | | | |
|---|---|---|---|
| 2006/0085407 A1* | 4/2006 | Kaminaga | A61B 6/032 |
| 2006/0173270 A1* | 8/2006 | Weiner | A61B 6/032 |
| | | | 600/407 |
| 2006/0264749 A1* | 11/2006 | Weiner | A61B 6/032 |
| | | | 600/437 |
| 2011/0110486 A1* | 5/2011 | Bouhnik | A61B 6/032 |
| | | | 378/8 |
| 2012/0281897 A1* | 11/2012 | Razifar | A61B 6/032 |
| | | | 382/131 |
| 2013/0259189 A1* | 10/2013 | Sakai | G01N 23/046 |
| | | | 378/4 |
| 2014/0149910 A1* | 5/2014 | Lee | A61B 6/465 |
| | | | 715/771 |
| 2014/0205171 A1* | 7/2014 | Zeng | G06T 11/005 |
| | | | 382/131 |
| 2015/0297157 A1* | 10/2015 | Mukumoto | A61B 6/5205 |
| | | | 378/15 |

* cited by examiner

*Primary Examiner* — Joel Lamprecht

(57) ABSTRACT

A system and method are provided for displaying information related to a medical imaging scan. Visual regions are shown on a display screen to indicate information of pending, current, and completed medical imaging scans. If additional correction time was utilized for particular table positions in a medical imaging scan, this information is shown on the display screen, in the form of icons, shading, or other visual representations. The medical imaging system may include positron emission tomography (PET) and single photon emission computed tomography (SPECT).

5 Claims, 13 Drawing Sheets

SYSTEM AND METHOD FOR DISPLAYING VARIABLE DURATION IMAGE SCANS

BACKGROUND OF THE INVENTION

The subject matter disclosed herein relates generally to imaging systems, and more particularly to a system and method for displaying information regarding medical imaging scans. Embodiments include an operator-interactive computer system interfaced with a medical imaging system.

Medical imaging systems perform scans of objects and provide displayed information to users through an operator console, which can be stationary or mobile. First forms of displayed information are images of the scanned object for a user to view. It has become more common in the medical field for images to be stored, distributed, and viewed in digital form using computer technology. In addition, users set up scan protocols and other scan related parameters before a scan, and then see details related to medical imaging scans on the displays of the operator console. Providing useful and easy to understand information to users is needed to improve efficiency and quality. Accordingly, it is desirable to provide users with improved systems and methods for displaying information related to variable duration image scans.

BRIEF DESCRIPTION OF THE INVENTION

In accordance with an embodiment, a computer system is provided, having a display, an input device, and a connection to an imaging system having a movable table, a method, comprising: receiving input to initiate an imaging scan, said scan includes multiple table positions; wherein, for each table position, the imaging scan includes an initial scan time and for at least one table position the medical imaging scan includes an additional correction time; and displaying a plurality of regions on the display, one region per table position in said scan; wherein the displayed regions for table positions that include additional correction time are larger than those displayed regions for table positions that do not include additional correction time.

The computer system may further perform the steps of issuing a command to the imaging system to begin the imaging scan; receiving count rate information from medical imaging system during the imaging scan; and displaying count rate information over time on the display within the region associated with a respective table position. The computer system may further perform the steps of issuing a command to the imaging system to stop the imaging scan for the current table position if count rate information reaches a threshold; displaying a first visual indicator in the displayed region related to the current table position if count rate information reaches a threshold; displaying a second visual indicator in the displayed region related to the current table position if count rate information does not reach a threshold; and wherein the first visual indicator is of a different shading, color, or shape from the second visual indicator. The computer system may further perform the steps of receiving gross patient motion information from the imaging system; and wherein displaying count rate information over time comprises displaying a first rate indicator for time segments without gross patient motion and displaying a second rate indicator for time segments with gross patient motion. The first rate indicator and second rate indicator are displayed differently by different color, shading, or shape.

Displaying a plurality of regions on the display can further comprise: displaying scan-uncompleted regions in a different color or shading from scan-completed regions. In addition, the computer system may further perform the steps of displaying only initial scan time information on the display related to the table position if no additional correction time is selected for the table position.

The computer system may further perform the steps of receiving motion related information from the imaging system; comparing motion related information with a threshold; if motion related information is higher than the threshold, instructing the imaging system to continue scanning into the additional correction time for the current table position; and if motion related information is lower than the threshold, instructing the imaging system to stop scanning for the current table position at the end of the initial scan time. The computer system may further perform the steps of displaying a count indicator in the region associated with the current table position; displaying an initial scan time section of the displayed region a different color or shading from the additional correction time section of the displayed region.

The computer system may further perform the steps of displaying a strength metric related to the received motion information. The displayed strength metric may be of a first shading or color if the motion related information is higher than the threshold; and the displayed strength metric may be of a second shading or color if the motion related information is lower than the threshold.

The computer system may further perform the steps of displaying at least one icon in the displayed region for the table position, wherein the icon is related to a type of motion. The displayed icon can be at least one of a lung icon or a heart icon. Further, the displayed icon may be of a first shading or color if the motion related information is higher than the threshold; and the displayed icon may be of a second shading or color if the motion related information is lower than the threshold.

The computer system may further perform the steps of receiving image information from the imaging system; reconstructing the image information into output images; and displaying the output images. The image information may comprise PET or SPECT data.

DETAILED DESCRIPTION OF THE INVENTION

Figure 1:
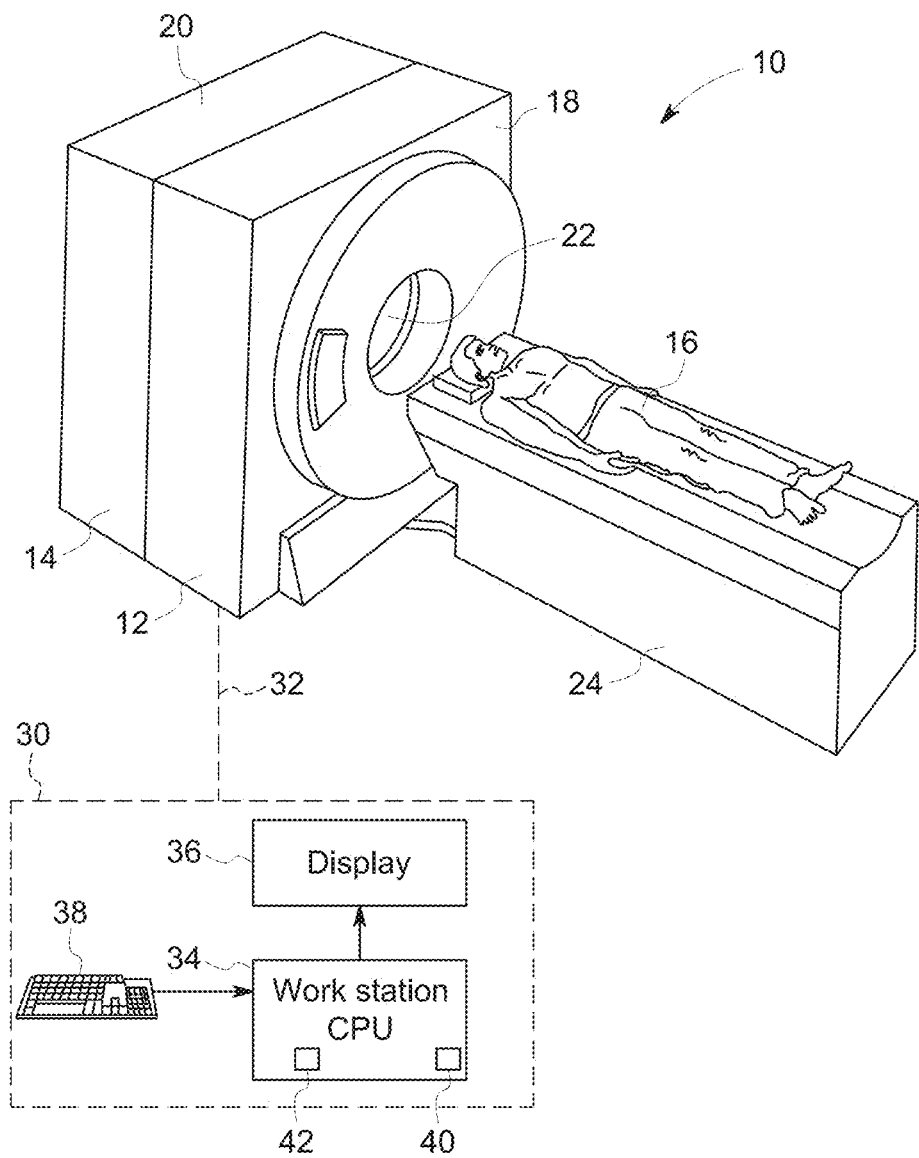
FIG. 1 is a pictorial view of an exemplary imaging system formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

FIG. 1 is a pictorial view of an exemplary imaging system formed in accordance with various embodiments. The imaging system 10 is a multi-modality imaging system that includes different types of imaging modalities, such as Positron Emission Tomography (PET), Single Photon Emission Computed Tomography (SPECT), Computed Tomography (CT), ultrasound, Magnetic Resonance Imaging (MRI) or any other system capable of generating diagnostic images. In the illustrated embodiment, the imaging system 10 is a PET/CT system. The various embodiments are not limited to medical imaging systems for imaging human subjects, but may include veterinary or non-medical systems for imaging non-human or inanimate objects.

Referring to FIG. 1, the multi-modality imaging system 10 includes a first modality unit 12 and a second modality unit 14. These units may be aligned along an axis, as shown in 10, or may co-habit a common space surrounding the patient such as having second modality unit 14 inside first modality unit 12 or vice versa. The two modality units enable the multi-modality imaging system 10 to scan an object or subject 16 in a first modality using the first modality unit 12 and to scan the subject 16 in a second modality using the second modality unit 14. The scans may optionally be simultaneous. Multi-modality imaging system 10 allows for multiple scans in different modalities to facilitate an increased diagnostic capability over single modality systems. In the illustrated embodiment, first modality unit 12 is a PET imaging system and second modality unit 14 is a CT system. Imaging system 10 is shown as including a gantry 18 that is associated with the PET imaging system 12 and a gantry 20 that is associated with the CT system 14. During operation, subject 16 is positioned within a bore, or central opening, 22, defined through imaging system 10, using, for example, a motorized table 24.

The imaging system 10 also includes an operator workstation 30. During operation, motorized table 24 moves subject 16 into central opening 22 of gantry 18 and/or gantry 20 in response to one or more commands received from operator workstation 30. During a scan, table 24 may move to a plurality of table positions to set the scanned subject 16 in a plurality of positions in relation to the gantry 20. Workstation 30 then sends signals to the first and/or second modality units 12 and 14 to both scan subject 16 and acquire emission data and/or CT data of subject 16. Workstation 30 may be embodied as a computer that is positioned near imaging system 10 and hard-wired to the imaging system 10 via a communication link 32. Workstation 30 may also be embodied as a portable computer such as a laptop computer or a hand-held computer that transmits information to, and receives information from imaging system 10. Optionally, the communication link 32 may be a wireless communication link that enables information to be transmitted to and/or from the workstation 30 to the imaging system 10 wirelessly. In operation, workstation 30 is configured to control the operation of the imaging system 10 in real-time. Workstation 30 is also programmed to perform medical image diagnostic acquisition and reconstruction processes described herein.

Workstation 30 includes a central processing unit (CPU) or computer 34, a display 36, and an input device 38. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, computer 34 executes a set of instructions that are stored in one or more storage elements or memory devices 42, in order to process information received from the first and second modalities 12 and 14. The storage elements may also store data or other information as desired or needed. The storage element may be in the form of an information source or a physical memory element located within the computer 34.

The imaging system 10 also includes an attenuation correction module 40 that implements various methods described herein. Attenuation correction module 40 may be implemented as a piece of hardware that is installed in the computer 34. Optionally, the attenuation correction module 40 may be implemented as a set of instructions that are installed on the computer 34. The set of instructions may be stand-alone programs, may be incorporated as subroutines in an operating system installed on the computer 34, may be functions in an installed software package on the computer 34, and the like. It should be understood that the various embodiments are not limited to the arrangements and instrumentality shown in the drawings.

The set of instructions may include various commands that instruct the computer 34 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
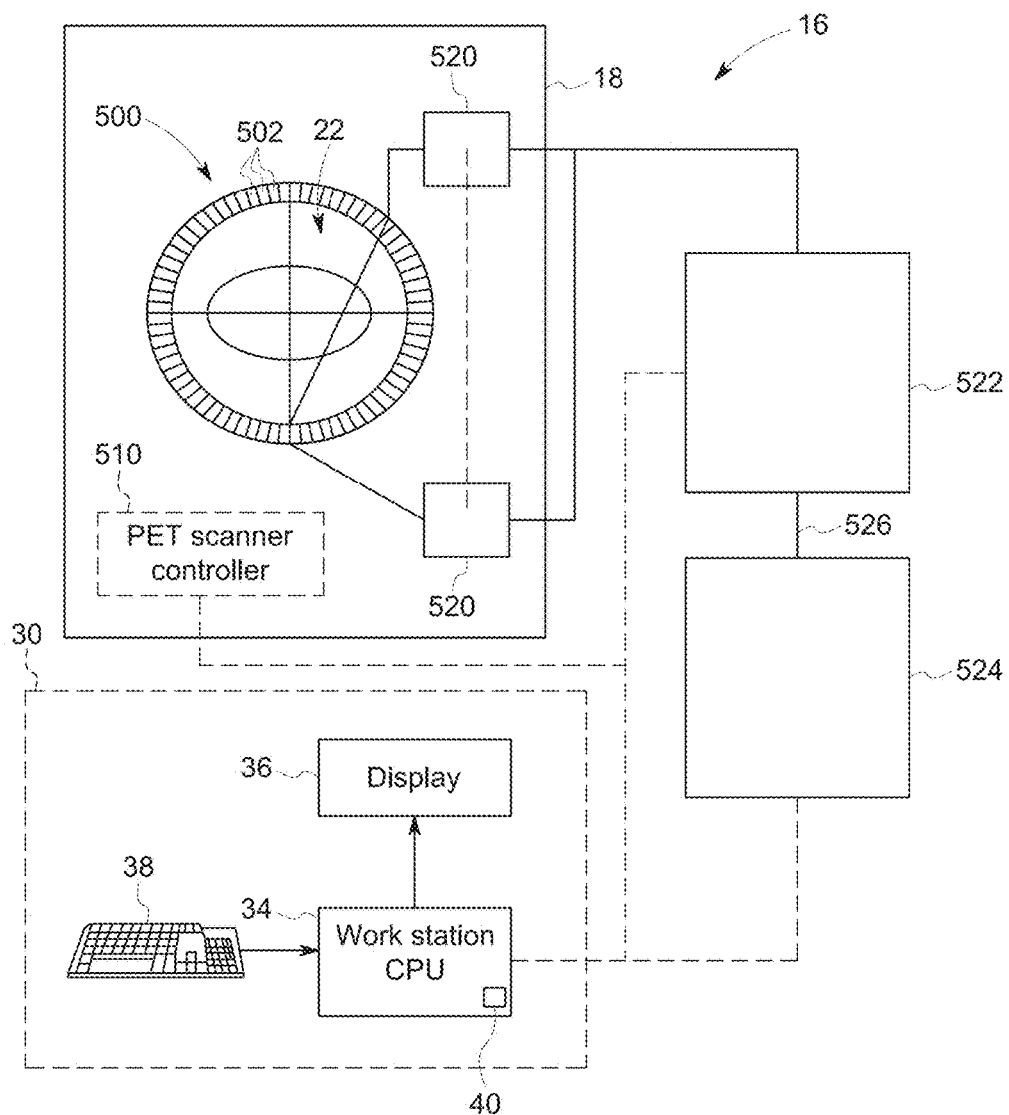
FIG. 2 is a block schematic diagram of a first modality unit shown in FIG. 1 in accordance with various embodiments.

FIG. 2 is a block schematic diagram of the first modality unit 12, e.g. the PET imaging system, shown in FIG. 1. PET system 12 includes a detector array 500 that is arranged as ring assembly of individual detector modules 502. The detector array 500 also includes the central opening 22, in which an object or patient, such as the subject 16 may be positioned, using, for example, the motorized table 24 (shown in FIG. 1). The motorized table 24 is aligned with the central axis of detector array 500. During operation, motorized table 24 moves the subject 16 into central opening 22 of detector array 500 in response to one or more commands received from operator workstation 30. More specifically, a PET scanner controller 510 responds to the commands received from operator workstation 30 through communication link 32. Therefore, the scanning operation is controlled from operator workstation 30 through PET scanner controller 510.

During operation, photons are emitted when positrons, emitted from a tracer within subject 16, collide with electrons inside a subject. When a photon collides with a scintillator on the detector array 400, the photon collision produces a scintilla on the scintillator. The scintillator produces an analog signal that is transmitted to an electronics section (not shown) that may form part of the detector array 500. The electronics section outputs an analog signal when a scintillation event occurs. A set of acquisition circuits 520 is provided to receive these analog signals. The acquisition circuits 520 process the analog signals to identify each valid event and provide a set of digital numbers or values indicative of the identified event. For example, this information indicates when the event took place and the position of the scintillation scintillator that detected the event.

The digital signals are transmitted through a communication link, for example, a cable, to a data acquisition controller 522. The data acquisition controller 522 performs scatter correction and/or various other operations based on the received signals. The PET system 12 may also include an image reconstruction processor 524 that is interconnected via a communication link 526 to data acquisition controller 522. During operation, image reconstruction processor 524 performs various image enhancing techniques on the digital signals and generates an image of the subject 16.

Figure 3:
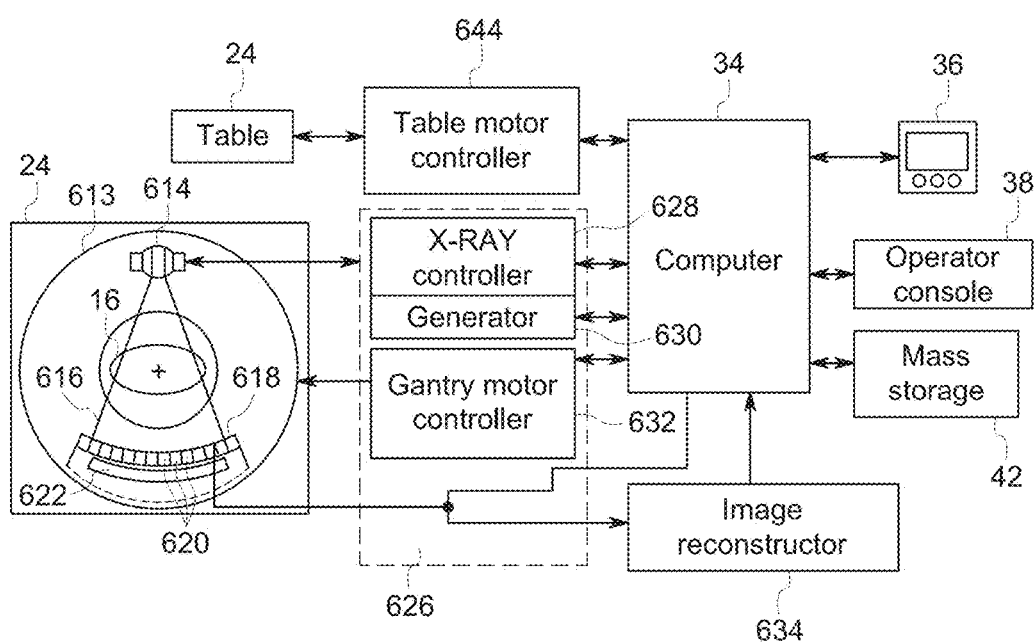
FIG. 3 is a block schematic diagram of a second modality unit shown in FIG. 1 in accordance with various embodiments.

FIG. 3 is a block schematic diagram of the second modality unit 14, e.g. the CT system, shown in FIG. 1. Gantry 20 has a rotary member 613 an x-ray source 614 that projects a beam of x-rays 616 toward a detector assembly 618 on the opposite side of the rotary member 613. A main bearing may be utilized to attach the rotary member 613 to the stationary structure of the gantry 20. X-ray source 614 includes either a stationary target or a rotating target. Detector assembly 618 is formed by a plurality of detectors 620 and data acquisition systems (DAS) 622. A collimator can be included at the detector end and/or at the x-ray emission end depending on the particular embodiment configuration. The plurality of detectors 620 sense the projected x-rays that pass through a subject 16, and DAS 622 converts the data to digital signals for subsequent processing. Each detector 620 produces an analog or digital electrical signal that represents the intensity of an impinging x-ray beam and hence the attenuated beam as it passes through subject 16. During a scan to acquire x-ray projection data, rotary member 613 and the components mounted thereon can rotate about a center of rotation.

Rotation of rotary member 613 and the operation of x-ray source 614 are governed by a control mechanism 626 of CT system. Control mechanism 626 can include an x-ray controller 628 and generator 630 that provides power and timing signals to x-ray source 614 and a gantry motor controller 632 that controls the rotational speed and position of rotary member 613. An image reconstructor 634 receives sampled and digitized x-ray data from DAS 622 and performs high speed image reconstruction. The reconstructed image is output to a computer 34 which stores the image in a computer storage device 42.

Computer 34 also receives commands and scanning parameters from an operator via operator input 38 that has some form of operator interface, such as a keyboard, mouse, touch sensitive controller, voice activated controller, or any other suitable input apparatus. Display 36 allows the operator to observe the reconstructed image and other data from computer 34. The operator supplied commands and parameters are used by computer 34 to provide control signals and information to DAS 622, x-ray controller 628, and gantry motor controller 632. In addition, computer 34 operates a table motor controller 644 which controls a motorized table 24 to position subject 16 and gantry 20.

Figure 4:
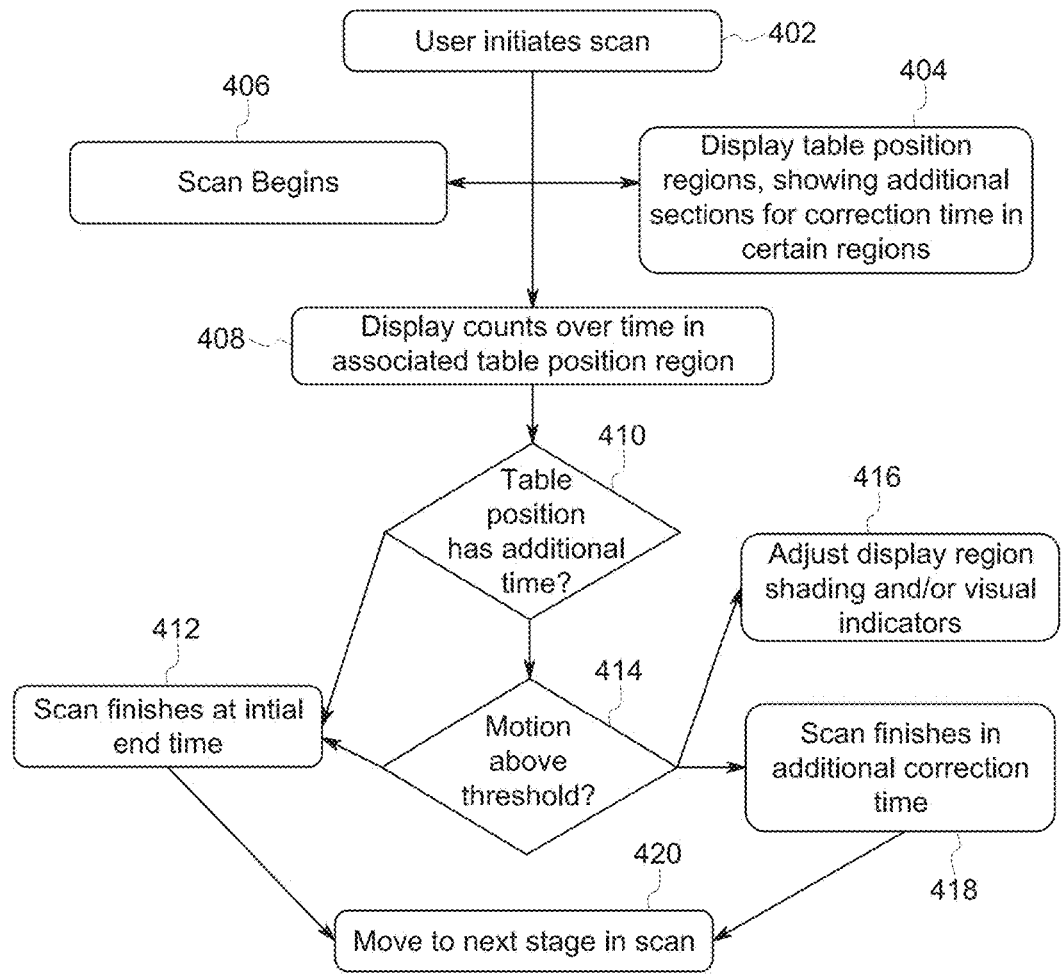
FIG. 4 is an imaging and display method in accordance with various embodiments.

FIG. 4 is an imaging and display method in accordance with various embodiments. FIG. 4 is utilized with emission data in an embodiment. This can include PET or SPECT data in various embodiments. FIG. 4 pertains to a technique for graphically displaying the emission scan times for emission scans that have dynamically determined end times.

In step 402, a user initiates a scan. Through the user interface on the operator console, a user initiates a scan that includes a scan protocol. The scan protocol may include the relevant details and settings needed to direct the imaging system to perform particular scans. The scan protocol can include specific times set for initial scan time and additional correction time. These values can be set per table position of the system. These values can be user set or set by the system. If set by the system, the values can be pre-programmed in certain scan protocols or chosen dynamically based on historical, context, and/or other analytical data. In addition, the user can enable or disable data driven gating (DDG) features for particular table positions through the user interface. The system can perform DDG without an external device to determine the gates of a cardiac or respiratory cycle, as examples. The additional correction time may be used to compensate for data loss due to motion in the patient. Thus, additional data may need to be acquired for motion correction. Additional correction time may also be referred to as additional scan time.

In step 404, the system displays table position regions, as shown more fully in FIGS. 5-13, in response to the scan being initiated. Each planned table position has a region displayed on the screen. Each table position region displayed includes an initial scan time section. Some table position regions displayed include one or more additional sections for correction time. Table position regions are shown in uncompleted shading as the scan has not been performed at this point. The display can also include visual indicators for the type of motion and/or type of scan initiated.

In step 406, the imaging system, such as shown in FIGS. 1-3, will begin the scanning of a subject on the table. Emission data counts of photon incidents are collected on image detectors and algorithms are used to reconstruct the emission data into images to be displayed to the user.

In step 408, the system displays counts over time in the associated table position region on the display. Current counts indicator 112 is an example of this display visual indicator. Counts may raise and lower over time, thus, an associated indicator may move up and down in the graph. This shows the user the current status and progress of the imaging scan at the current table position. If not enough or too many counts are being displayed, the user may be indicated as to an issue with the patient or system they can correct before proceeding. Additional visual indicators may also be static or dynamically displayed during this step as indicated below in relation to further figures.

In step 410, the system makes a determination whether additional correction time has been selected for this table position. This was selected by the user or the system before the scan was initiated in an embodiment. It may be set at another time in an alternative embodiment. The additional time is additional correction time such as additional correction time 104.

In step 412, if additional correction time or data driven gating was not selected for the particular threshold (from step 410), the scan finishes at initial end time. In addition, if there was additional correction time, but motion was below a threshold (from step 414), the scan finishes at initial end time. Examples of these scenarios, respectively, are shown in the first two table position regions 100 of FIG. 5.

In step 414, the system makes a determination if motion is above or below a threshold. The threshold is set in the system and is related to an image quality rating. The motion could be cardiac motion, respiratory, and/or gross patient motion in varying examples. In addition, step 414 can verify if counts are above a threshold, see FIGS. 7 and 10 for example. If below the threshold, the system moves to step 412. If above the threshold, the system moves to steps 416 and 418.

In step 416, the system adjusts the display region shading and/or visual indicators as a result of the imaging activity. Visual indicators may change in shape, value, shading, or color. The counts visual indicator also adjusts in terms of length and direction. When the system has started its scan at one table position, the displayed table position region shading can be changed from uncompleted to in-progress. When the system has completed its scan at the table position, the displayed table position region shading can be changed from in-progress to completed. This is feedback to the user related to the workflow and status of the imaging system. The adjustments are discussed further in reference to FIGS. 5-13.

In step 418, the system completes it scan during the additional correction time. This may use some or all of the additional correction time, which is visualized as mentioned with reference to step 416.

In step 420, the system moves to the next stage in the scan process. This can be the next table position for scanning if there are remaining table positions to scan. Otherwise, the system may complete its scan and reconstruct the image data for saving to memory and displaying to a user. The system may reconstruct the image data using quiescent data. This can remove motion affected information and improve image quality.

Figure 5:
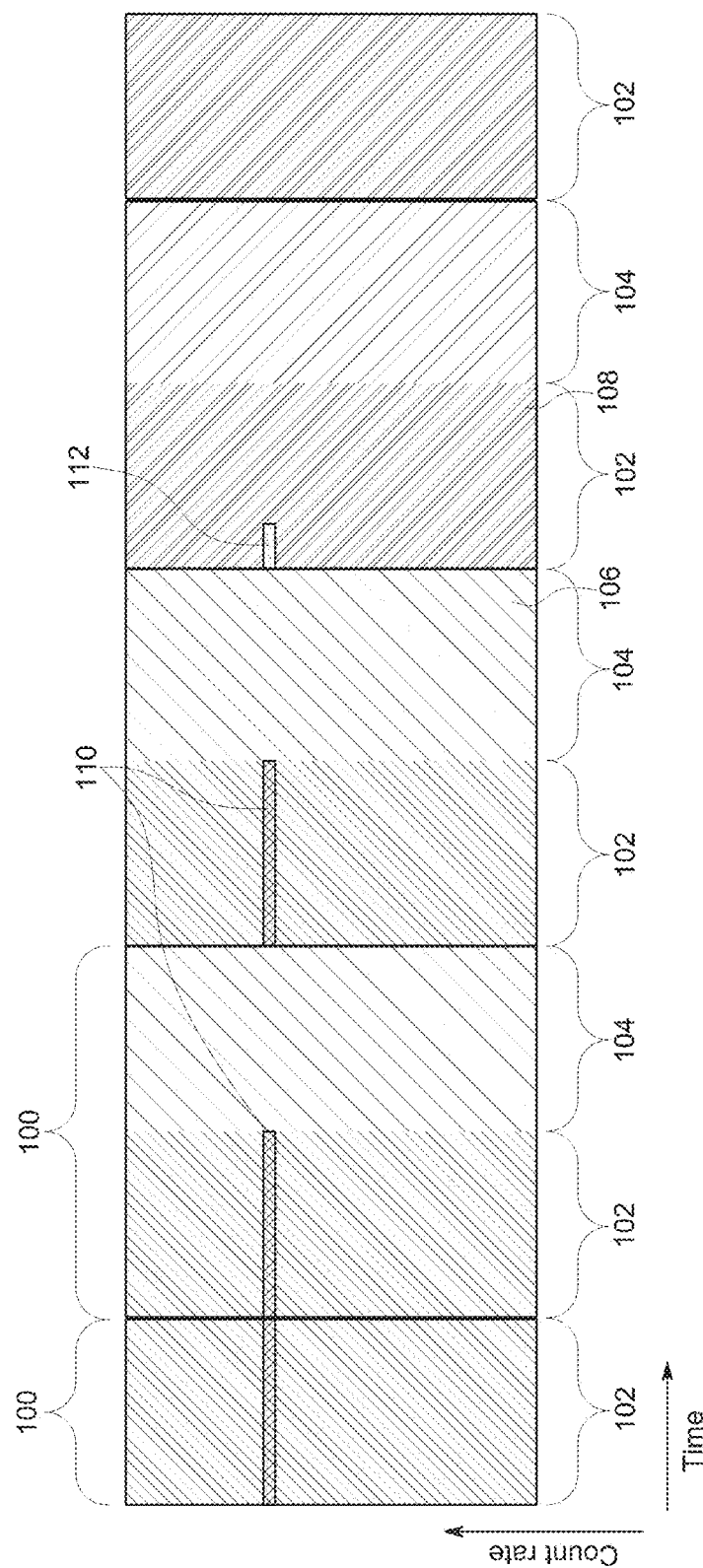
FIG. 5 is a display view of an in-progress imaging scan in accordance with various embodiments.

FIG. 5 is a display view of an in-progress imaging scan in accordance with various embodiments. The system displays table position regions 100 on the display. In the embodiment of FIG. 5, five table position regions are displayed. Regions 100 show a count rate versus time graph. In specific, count rate is shown by the vertical axis, and time is shown by the horizontal axis. Vertical axis count numbers may be shown in alternate embodiments. Time axis count numbers may be shown in alternate embodiments.

Each region includes an initial scan time 102. Some regions include an additional correction time 104. In the embodiment of FIG. 5, the second, third, and fourth table positions include additional correction time. Additional correction time 104 shows how much the scan could be shorted based on various factors, discussed further below. Initial scan time 102 and additional correction time 104 are displayed differently to a user, based on color, shading, outlined dashes or outlined lines. In the embodiment of FIG. 5, shading is used to show a user where the initial end time 102 ends and where additional correction time begins. Thin lined shading indicates additional correction time 104 in an embodiment. Wide lined shading indicates initial scan time 102 in an embodiment. These may be signified by colors in an alternate embodiment.

FIG. 5 shows an in-progress scan. The scan is currently completing the fourth bed position. Thus, the shading and/or color of the first three table positions, completed regions 106, is different than the final two, in-progress regions 108, on the display of the operator console. This helps the user understand what has happened in the past, what is happening at the present, and what will likely happen in the future. Thus, while the emission scan is in progress, the user interface dynamically displays various scan parameters. In the embodiment of FIG. 5, there are two shading options for regions, completed regions 106 and in-progress regions 108. In an alternate embodiment, there may be three shading options, one for completed regions, one for in-progress regions, and one for un-scanned regions. Completed regions may be called scan-completed regions. Uncompleted regions may be called scan-uncompleted regions.

Current count indicator 112 indicates the current amount of detection counts coming from the image detectors in the imaging system at the present moment. Completed count indicators 110 shows the count values received to the operator console during the first three table positions. Current count indicator 112 and completed count indicators 100 are drawn as horizontal bars in FIG. 5. In practice, these may have variations and fluctuations up and down during a scan as the count rate alters. Thus, the straight horizontal nature of said indicators may be in one embodiment, with other visual representations of said indicators in varying embodiments.

In all three circumstances of the first three table positions, the scan at the first three table positions was completed during initial scan time 102. If, for example, initial scan time 102 is two minutes and additional correction time 104 is three minutes, the imaging scan is already six minutes ahead of how long it could have taken if motion or other factors were involved to require the additional scan time. Both initial scan time 102 and additional correction time 104 can be set by a user or set by the system as discussed throughout herein.

Figure 6:
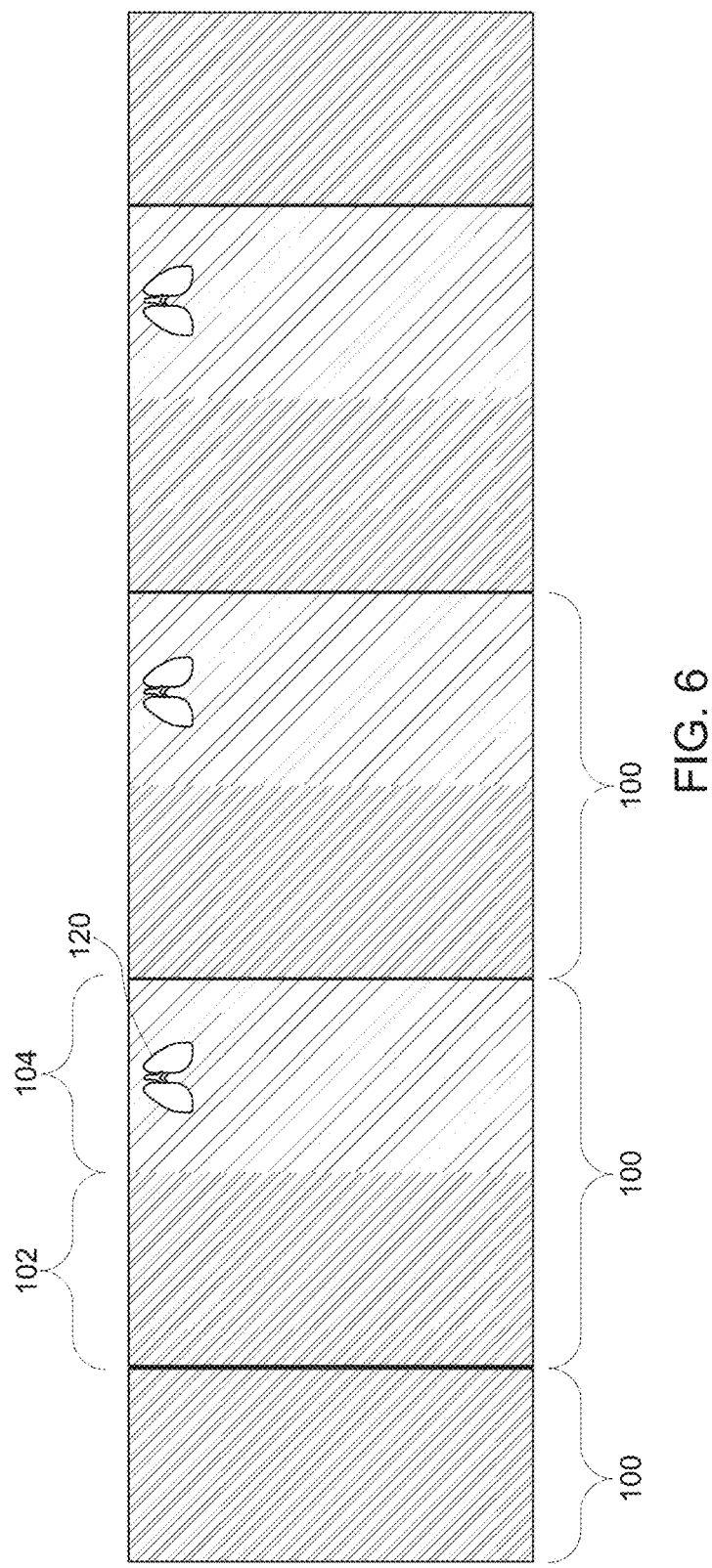
FIG. 6 is a display view of a respiratory motion affected imaging scan in accordance with various embodiments.

FIG. 6 is a display view of a respiratory motion affected imaging scan in accordance with various embodiments.

Table position regions 100 includes initial scan time 102 and may include additional correction time 104. Initial scan time 102 and additional correction time 104 are shaded differently in this embodiment to show the user what time for sure will occur, initial scan time 102, and what additional correction time 104 may be needed. The system displays lung visual indicator 120 on the display. This helps a user quickly understand that the additional correction time 104, if needed, is related to respiratory motion. Thus, if lung respiratory motion affects the imaging scan enough in initial scan time 102, the system may utilize additional correction time 104 in order to get enough data to best represent the subject being scanned. Lung visual indicator 120 can be animated during the time that its region is in-progress scanning, appearing as beating lungs to a user viewing the display. Visual indicators can be an icon, image, or other visual indicator known in the art. Visual indicators may be two dimensional (2D), three dimensional (3D), or four dimensional (4D).

Figure 7:
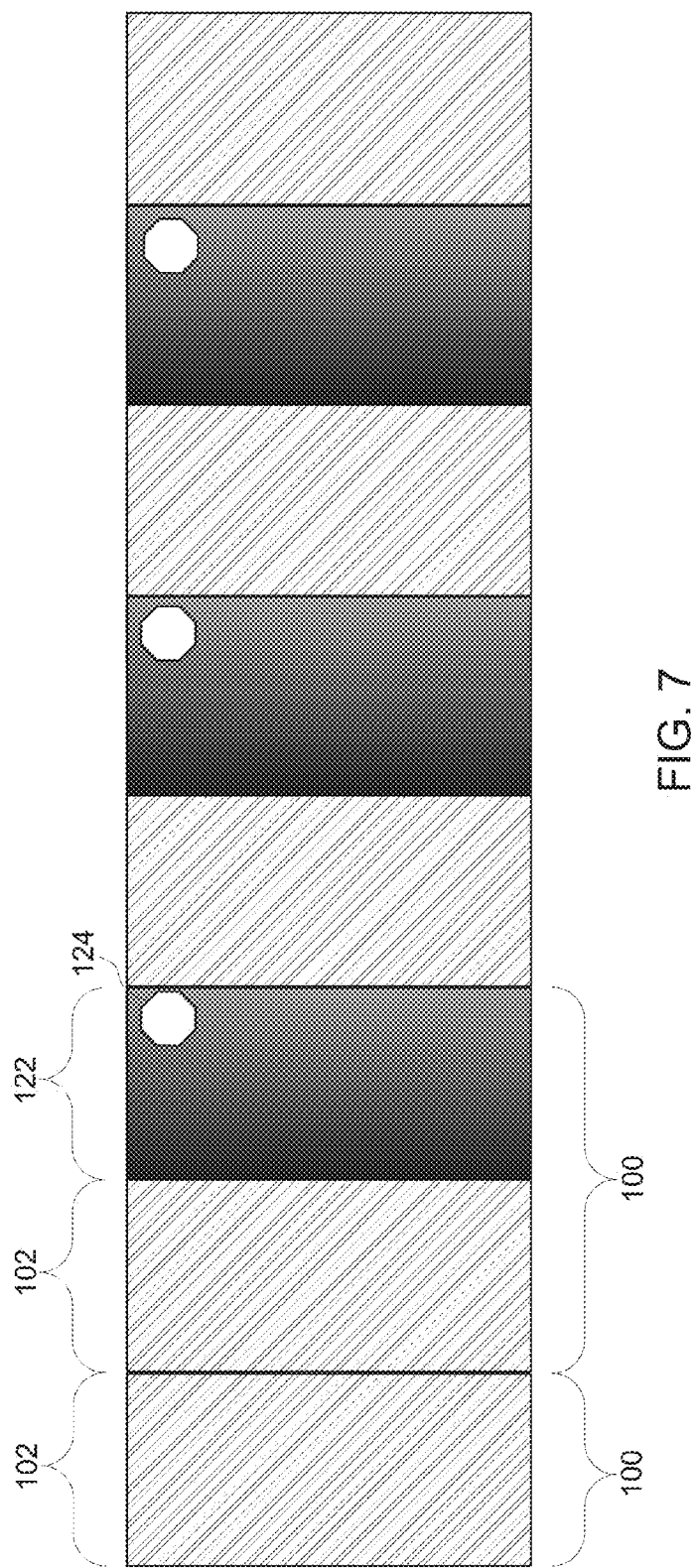
FIG. 7 is a display view of stop on counts imaging scan in accordance with various embodiments.

FIG. 7 is a display view of stop on counts imaging scan in accordance with various embodiments. Initial scan times 102 are included in all table position regions 100. The second, third, and fourth regions include gradient correction time 122. Gradient correction time 122 is additional correction time, if needed. Gradient correction time 122 is shown as gradient because the count rate indicator may stop at any point in that section. The system displays stop-on-counts visual indicator 124 to show the user a visual explanation behind the system decision making of when to stop the scan in specific table positions. This helps the user understand how and why the imaging system is operating during an imaging scan. Stop-on-counts imaging includes a threshold number of counts that each table position needs to acquire for quality image reconstruction. Thus, the system will complete scan for the second, third, and fourth table positions once that threshold has been met for each table position. The count threshold may be a uniform number across all three table positions, or be set for each individual table position. Stop-on-counts visual indicator is shown as a stop sign related icon in FIG. 7. Other images or icons may be used based on user preferences or system requirements.

Figure 8:
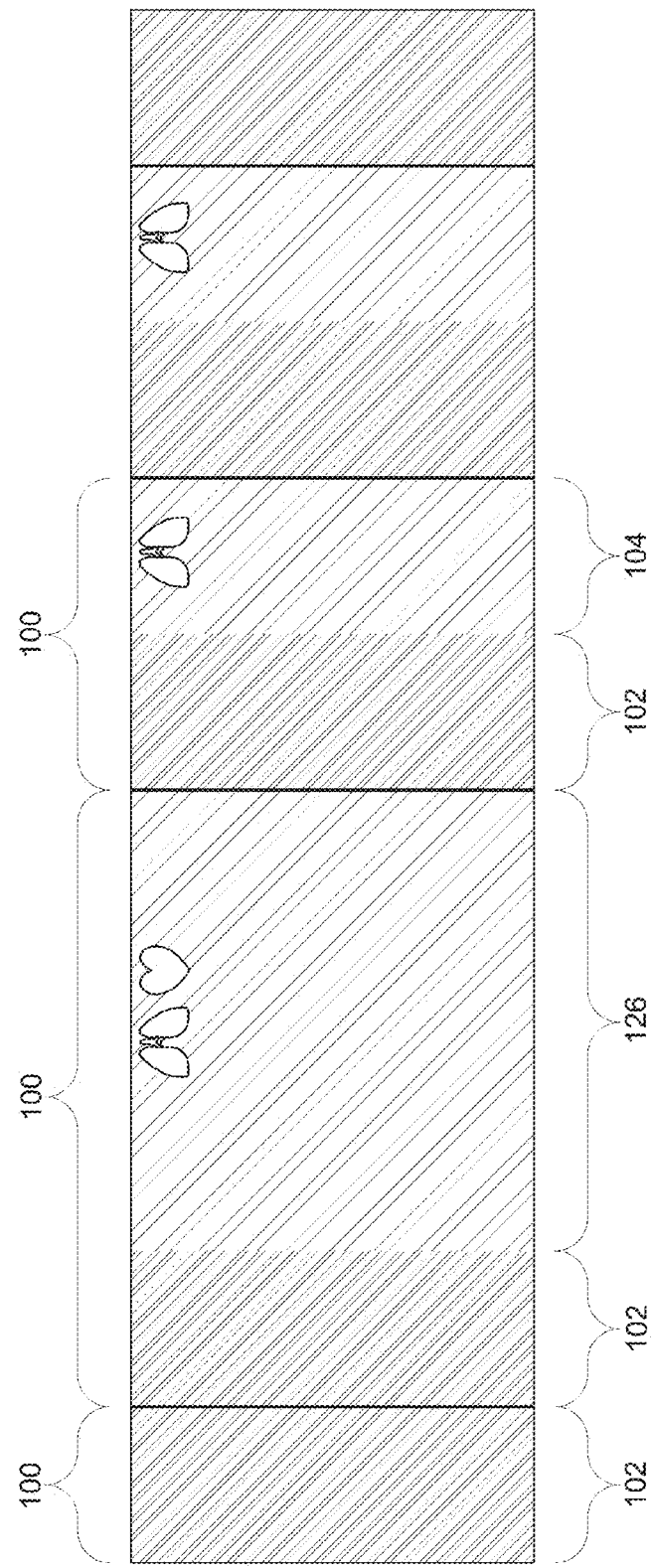
FIG. 8 is a display view of respiratory and cardiac motion affected imaging scan in accordance with various embodiments.

FIG. 8 is a display view of respiratory and cardiac motion affected imaging scan in accordance with various embodiments. FIG. 8 shows a dual gating embodiment. The second table position and its associated table position region 100 may be affected by both respiratory and cardiac motion. Thus, dual gating correction time 126 is shown in the second frame. Dual gating is indicated to the user by use of the lung indicator and heart indicator on the screen. Both may animate during the scanning of the second table position. Dual gating correction time 126 may be longer than additional correction time 104 because the data collected may need to be dual quiescent. Both the heart and lung movement should be minimal for quality image data reconstruction. Dual gating correction time 126 may include solid shading or gradient sharing if not all of the dual gating correction time may be needed.

Figure 9:
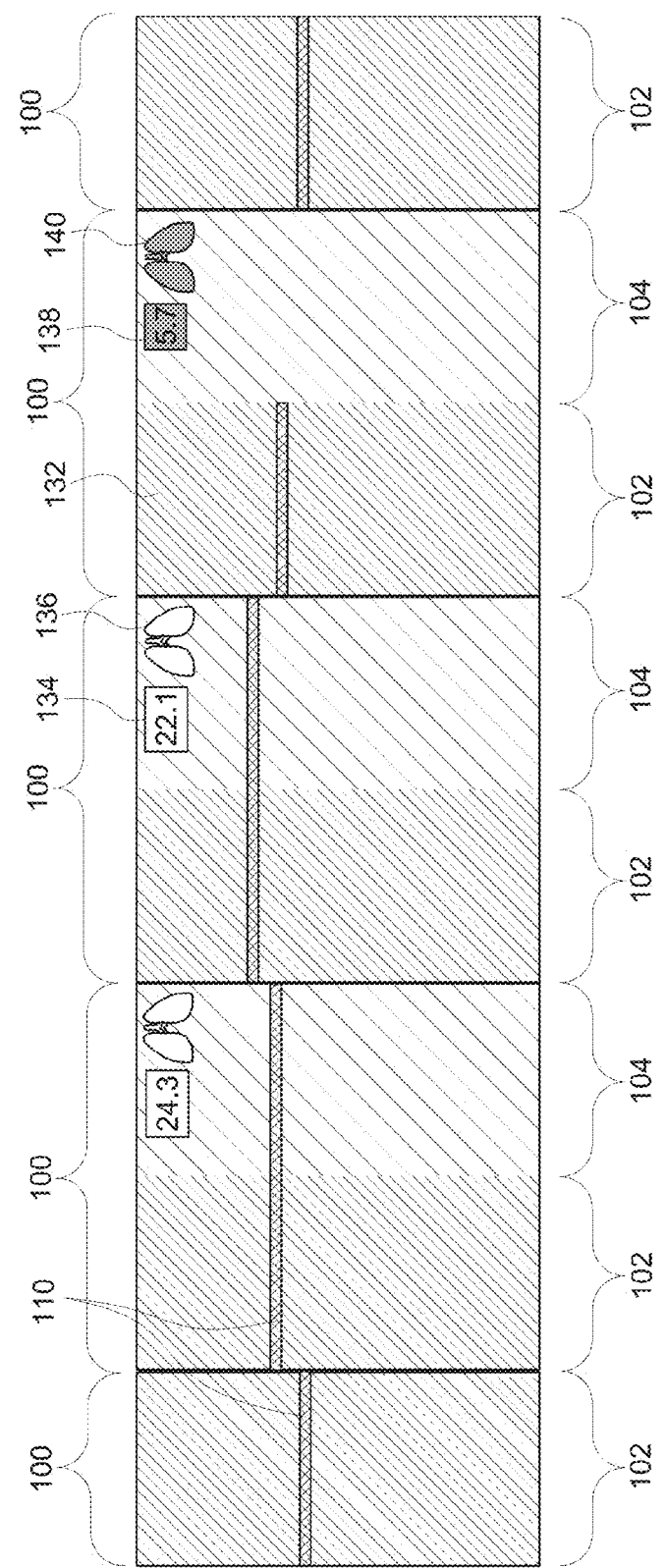
FIG. 9 is a display view of a completed respiratory motion affected imaging scan with variable scan durations in accordance with various embodiments.

FIG. 9 is a display view of a completed respiratory motion affected imaging scan with variable scan durations in accordance with various embodiments. Five table position regions 100 are shown. The scan is completed, so completed count indicators 110 are shown in all five table position regions 100. All regions 100 include initial scan time 102. The second, third, and fourth regions 100 include additional correction time 104. The user is alerted to potential for respiratory motion affecting the imaging scan by the lung visual indicators. In the fourth table position region, the system was able to dynamically shorten the scan time when a significant amount of respiratory motion is not detected. This speeds up the scan for the subject and user. In an embodiment, the subject can be a medical patient and the user a medical professional.

High-motion lung indicator 136 indicates that the threshold of step 414 was reached and so additional correction time 104 was needed. Low-motion lung indicator 140 indicates that the threshold of step 414 was not reached so additional correction time 104 was not needed, for the fourth table position for example. Motion lung indicator 136 and still lung indicator 140 are of different color, shading, shape, or other alterations so as to appear different to the user.

High-motion strength metric 134 and low-motion metric 138 show a metric to the user relating to the amount of motion at the specific table position; in this case the motion is caused by movement related to the lungs. The amount of motion is compared with a threshold, at step 414 for example. It could be, in this particular embodiment, a threshold of 15. Motion can be measured in different ways; FIG. 9 shows just one embodiment. Low-motion strength metric 138 and high-motion strength metric are of different color, shading, shape, or other alternatives so as to appear different to the user. In addition, metrics 134 and 138 may not be shown as numbers, but instead may be bars, dial-type, numbers of dots, or other visual indicators.

Figure 10:
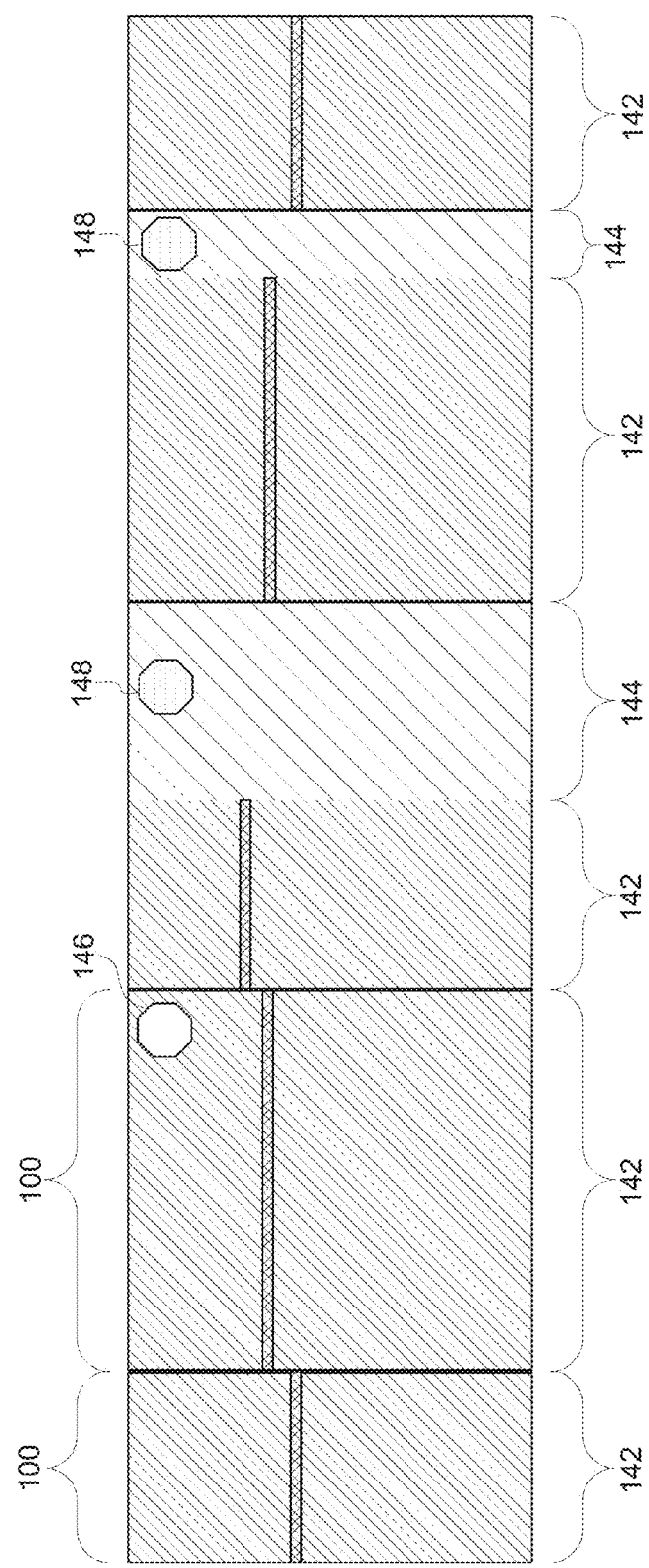
FIG. 10 is a display view of a completed stop on counts imaging scan in accordance with various embodiments.

FIG. 10 is a display view of a completed stop-on-counts imaging scan in accordance with various embodiments. FIG. 10 shows a completed imaging scan with five table positions. Table position regions 100 are displayed on the screen. All regions 100 include a stop-on-counts time 142. The third and fourth regions also display a saved time 144. Saved time 144 indicates the amount of time that was saved because the imaging scan stopped without going to the full planned scan time. Thus, the imaging scan is sped up for the user and the subject. The scans completed early at the third and fourth table positions because the count rate had hit a threshold related to image quality.

Standard stop indicator 146 is displayed when the scan did not terminate early at the specific bed position. Early stop indicator 148 is displayed when the scan did terminate early at the specific bed position. Standard stop indicator 146 and early stop indicator 148 are of different color, shading, shape, or images to show difference to the user. Thus, the system changes the display to show what happened during the imaging scan, which helps alter future user behavior as well as understanding of the imaging data.

Figure 11:
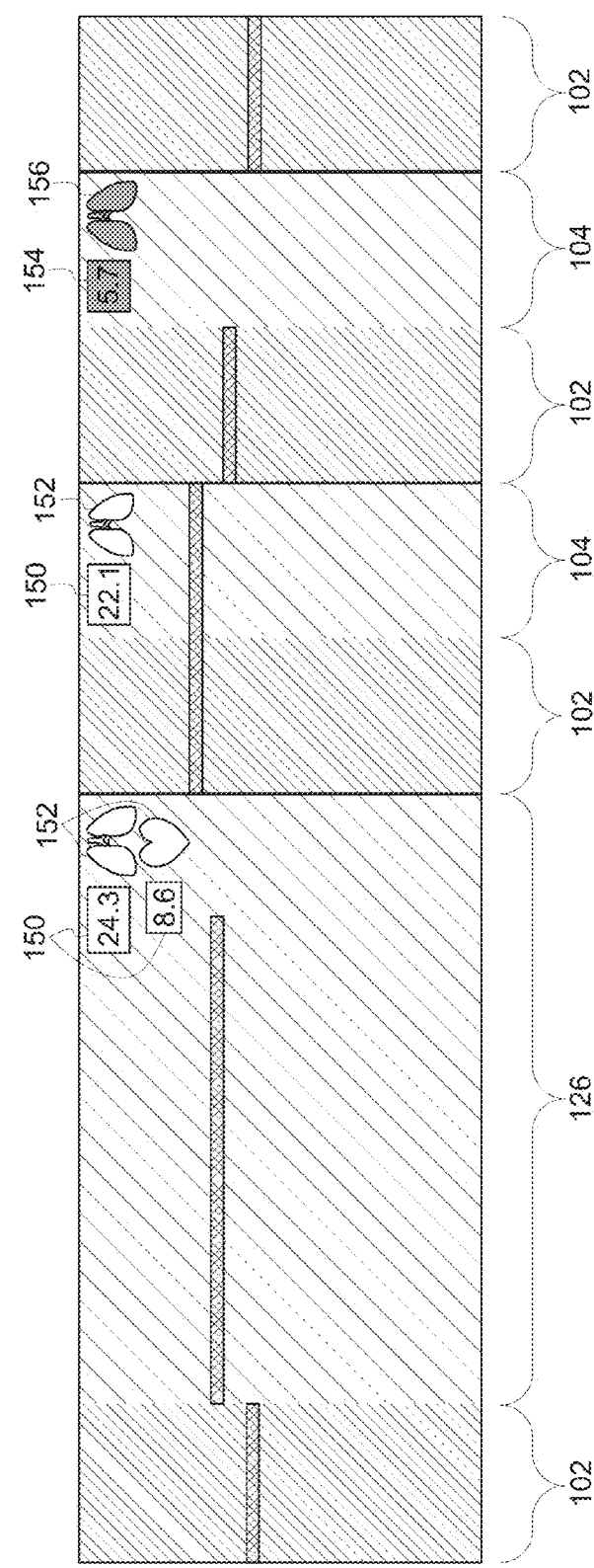
FIG. 11 is a display view of a completed imaging scan affected by respiratory and cardiac motion in accordance with various embodiments.

FIG. 11 is a display view of a completed imaging scan affected by respiratory and cardiac motion in accordance with various embodiments. Four table positions are shown in the embodiment of FIG. 11. A completed dual gating imaging scan has visual representation on the display, as driven by the system. High motion strength metrics 150 and high-motion visual indicators 152 are displayed for regions that needed to use additional correction time 104 or dual gating time 126. Low-motion strength metric 154 and low-motion visual indicator 156 are displayed for regions that did not need to use additional correction time 104 or dual gating time 126. Lung motion may affect the first, second, and third table positions. Heart motion may affect the first table position.

Figure 12:
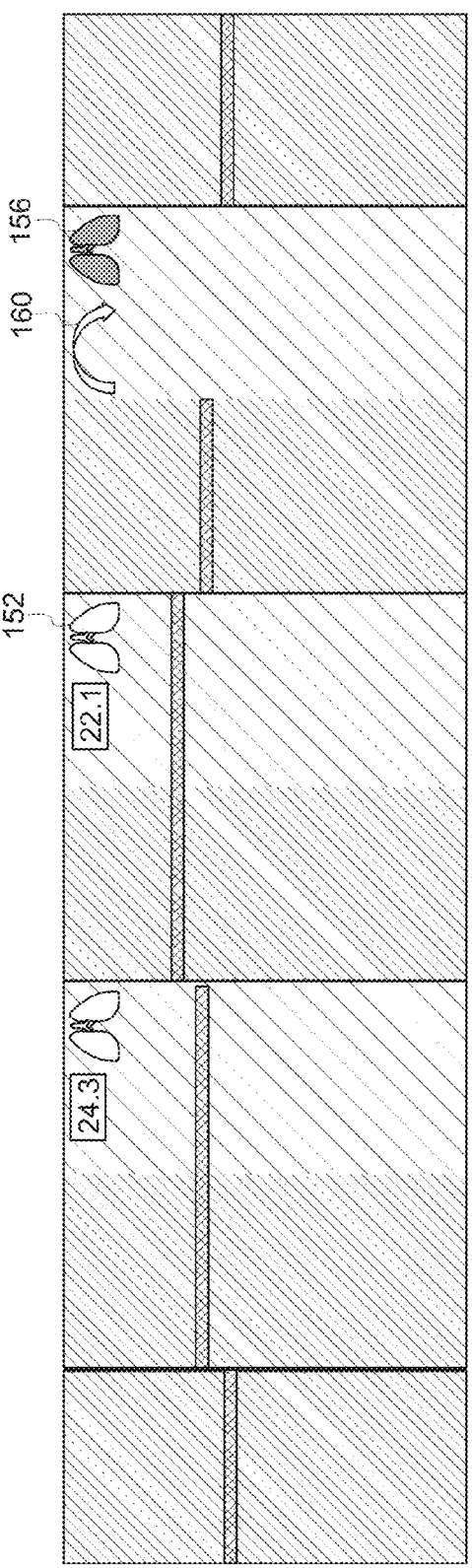
FIG. 12 is a display view of a completed imaging scan including user interaction in accordance with various embodiments.

FIG. 12 is a display view of a completed imaging scan including user interaction in accordance with various embodiments. In this embodiment, the system displays a user-stop visual indicator 160 in the fourth table position region. This is shown as a curved arrow in an embodiment, but may be shown by other forms of images or icons in varying embodiments. The user-stop visual indicator 160 indicates that the user issued a command from the operator console to stop the scan at a particular table position, either without needing additional correction time or just stopping at a certain point to speed up the process of scanning or for other reasons. For some reason, the user stopped the scan, and the system can display a related indicator. High-motion indicator 152 is shown. Motion-not-checked indicator 156 is displayed to indicate that motion was not checked for this table position even though it was programmed in for the initial scan or scan protocol, as in step 402. Because motion was not checked, no motion strength metric is shown in the fourth region. High-motion indicator 152 and motion-not-checked indicator 156 are of different color, shape, or image to show differing results to the user. This helps user understanding of the operation of the system during an imaging scan. The user may perform such a user-stop if a certain table position is not related to a region of interest or is not high priority, as examples.

Figure 13:
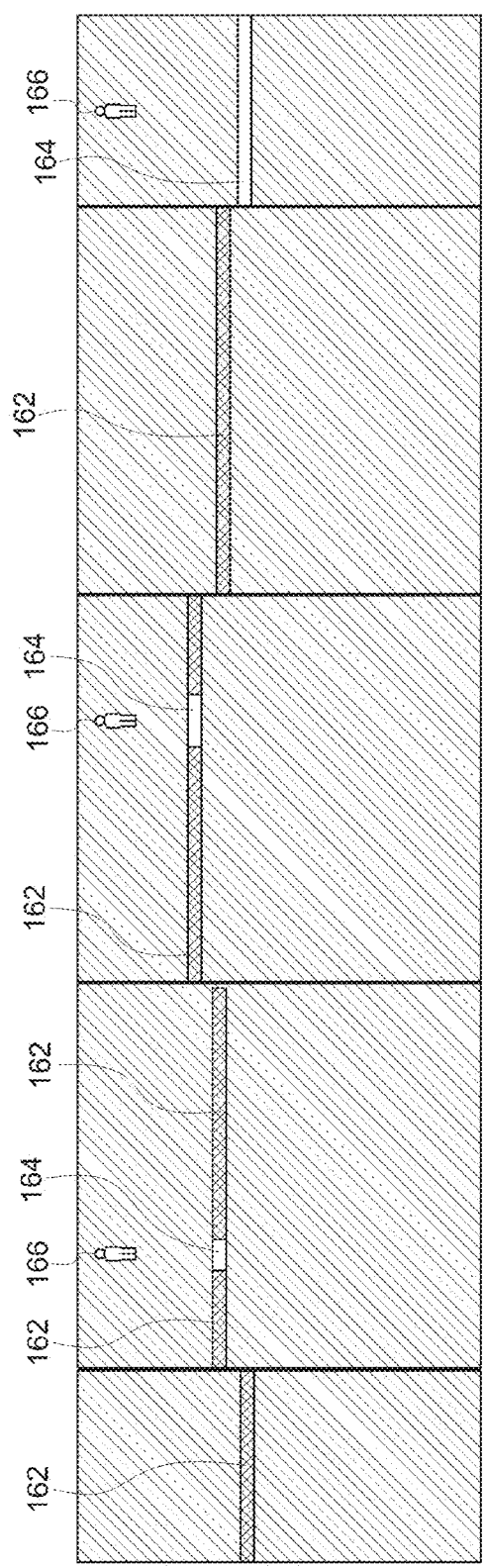
FIG. 13 is a display view of a completed imaging scan affected by gross patient motion in accordance with various embodiments.

FIG. 13 is a display view of a completed imaging scan affected by gross patient motion in accordance with various embodiments. Gross patient motion is motion not caused by a specific organ, and can encompass any additional movement the user initiates of the head, arms, torso, legs, and other body parts. Scans may take a while, and users may get restless. Or a user may have to scratch an itch or one of many other reasons to move during an imaging scan. Gross patient motion can be detected by the imaging system and related information can be sent to the system for processing and displaying of related information to a user.

Useful count indicator 162 shows count rates during times when gross patient motion is not negatively affecting the scanned image data. Motion count indicator 164 shows count rates during times when gross patient motion is negatively affecting the scanned image data. Useful count indicator 162 is shown as of different color or shading than motion count indicator 164. This alerts the user to sections of the scan where the patient may have been moving. Scanned image data taken during the times of motion count indicator 164 may be discarded by the system to improve image quality during image reconstruction. Additionally, a gross patient motion indicator 166 may be displayed in table position regions that had gross patient motion. This alerts the user to the specific type of motion that may have caused issues during the type of scan. Gross patient motion indicator 166 is shown as a human icon in the present embodiment, but may be represented by other images, shapes, or icons. Detecting and correcting data for gross patient motion may include principal components analysis (PCA) technique.

Benefits of the system and methods include better understanding to a user of the system on how the system is operating with respect to a medical imaging scan. The system and method succinctly informs the operator of multiple parameters that affect scanning. If the system performs a smart auto-stop because of threshold or motion correction factors, the user can understand the reasons for this with more precision. In addition, scans can be sped up, benefiting patients, clinicians, and hospitals.

As used herein, a set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system, comprising;
a gantry comprising image detectors;
a movable table for positioning a subject of an imaging operation;
an operator console comprising an input device and a display apparatus; and
a computer processor for executing instructions to:
receive input from the input device to initiate an imaging scan, said scan includes multiple table positions; wherein, for each table position, the imaging scan includes an initial scan time, where the initial scan time is the minimum amount of time needed to acquire data at each table position, and for at least one of the multiple table positions, the imaging scan includes an additional scan time, where the additional scan time includes additional time required to compensate for data loss due to patient motion at the at least one table position; and display a display view of an in-process imaging scan, the display view including a plurality of regions, one region per table position in said scan; wherein the displayed regions for table positions that include additional correction time are larger than those displayed regions for table positions that do not include additional correction time, wherein the additional correction time is displayed differently than the initial scan time in display view based on at least one of color, shading, outlined dashes or outlined lines.

2. The system of claim 1, the computer processor further:

issuing commands to the gantry and table to begin the imaging scan;

receiving count rate information from the image detectors during the imaging scan, where the count rate information is based on emission data; and displaying count rate information over time on the display within the region associated with a respective table position.

3. The system of claim 2, the computer processor further:

issuing a command to the gantry to stop the imaging scan for the current table position if count rate information reaches a threshold;

displaying a first visual indicator in the displayed region related to the current table position if count rate information reaches a threshold;

displaying a second visual indicator in the displayed region related to the current table position if count rate information does not reach a threshold; and wherein the first visual indicator is of a different shading, color, or shape from the second visual indicator.

4. The system of claim 1, the computer processor further:

receiving count information and motion related information from the image detectors, where the count information is based on emission data;

displaying a count indicator in the region associated with the current table position;

comparing motion related information with a threshold, where the motion related information is based on patient motion;

if motion related information is higher than the threshold, instructing the image detectors to continue scanning into the additional scan time for the current table position;

if motion related information is lower than the threshold, instructing the image detectors to stop scanning for the current table position at the end of the initial scan time;

displaying an initial scan time section of the displayed region a different color or shading from the additional scan time section of the displayed region.

5. The system of claim 4, wherein:

motion related information is generated as a response to detection of respiratory or cardiac motion.

* * * * *